(12) United States Patent
DeChiara et al.

(10) Patent No.: US 6,908,744 B1
(45) Date of Patent: Jun. 21, 2005

(54) METHODS OF STIMULATING CARTILAGE FORMATION

(75) Inventors: Thomas M. DeChiara, Katonah, NY (US); Robert Kimble, deceased, late of Hopewell Junction, NY (US); by Carrie A. Kimble, legal representative, Hopewell Junction, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 43 days.

(21) Appl. No.: 10/221,599

(22) PCT Filed: Feb. 20, 2001

(86) PCT No.: PCT/US01/05473

§ 371 (c)(1),
(2), (4) Date: Oct. 8, 2003

(87) PCT Pub. No.: WO01/68812

PCT Pub. Date: Sep. 20, 2001

Related U.S. Application Data

(60) Provisional application No. 60/189,216, filed on Mar. 14, 2000.

(51) Int. Cl.[7] ............................. C12Q 1/02; C12Q 1/00; G01N 33/53
(52) U.S. Cl. ........................... 435/29; 435/7.1; 435/7.2; 435/4
(58) Field of Search ............................. 435/29, 7.1, 7.2, 435/4

(56) References Cited

U.S. PATENT DOCUMENTS 5,843,749 A    12/1998  Maisonpierre et al. ....... 435/194
5,846,770 A  * 12/1998  LaVallie et al. ............ 435/69.1
6,586,251 B2 *  7/2003  Economides et al. ........ 435/463
6,596,541 B2 *  7/2003  Murphy et al. ............. 435/463

OTHER PUBLICATIONS

Oldridge, M., et al., 2000, "Dominant mutations in ROR2, encoding an orphan receptor tyrosine kinase, cause brachydactyly type B", Nat Gen 24:275–278.

Saldanha, J., et al., 1998, "Indentification of a frizzled–like cysteine rich domain in the extracellular region of developmental receptor tyrosine kinases", Prot Sci 7:1632–1635.

Takeuchi, S., et al, 2000, "Mouse Ror2 receptor tyrosine kinase is required for the heart development and limb formation", Genes to Cells 5:71–78.

DeChiara, T.M., 2000, "Ror2, encoding a receptor–like tyrosine kinase, is required for cartilage and growth plate development", Nat Gen 24:271–274.

* cited by examiner

*Primary Examiner*—Louise N. Leary
(74) *Attorney, Agent, or Firm*—Valeta Gregg, Esq.

(57) ABSTRACT

The disruption of the murine ROR2 gene leads to profound skeletal abnormalities, with essentially all endochondrally derived bones foreshortened and/or misshapen, albeit to differing degrees. ROR2 is selectively expressed in the chondrocytes of all developing cartilage anlagen, where it plays a critical role during initial growth and patterning, as well as subsequently in the proliferating chondrocytes of mature growth plates, where it is required for normal expansion. As ROR2 appears to play a critical role in cartilage formation and it may be useful in developing therapeutic strategies to treat diseases of cartilage such as osteoarthritis.

31 Claims, 14 Drawing Sheets

Figure 2B.
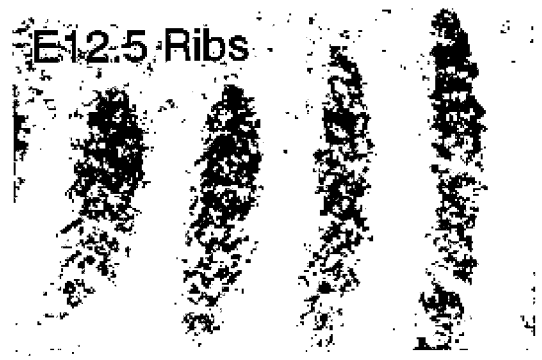
Figure 2C.
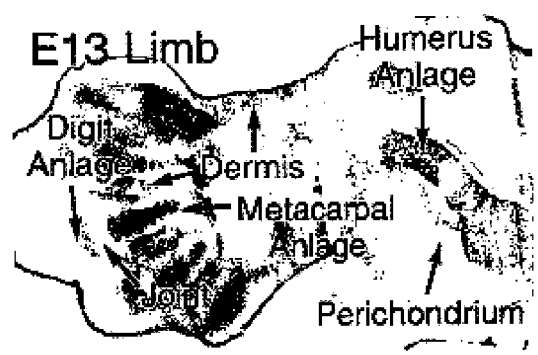
Figure 2D-1.          Figure 2D-2.
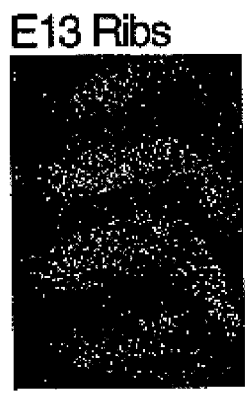          

Figure 2E.
Figure 2F.
Figure 2G.
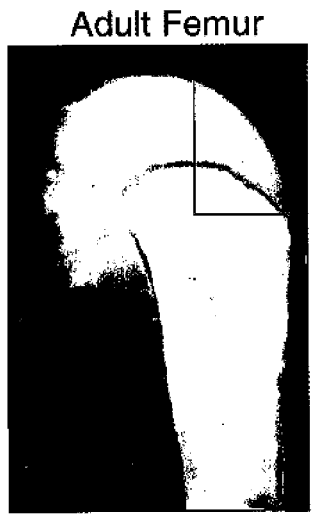
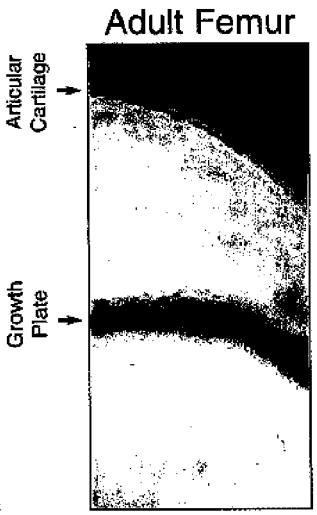
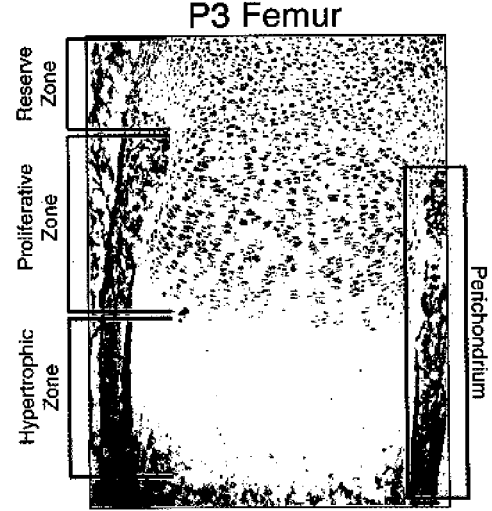

Figure 4I.
Figure 4J.
Figure 4K.
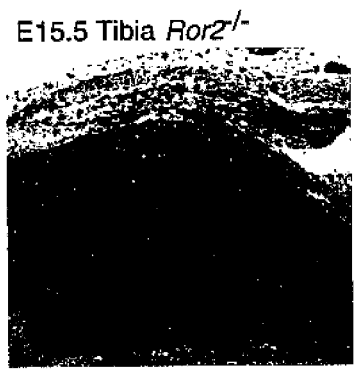
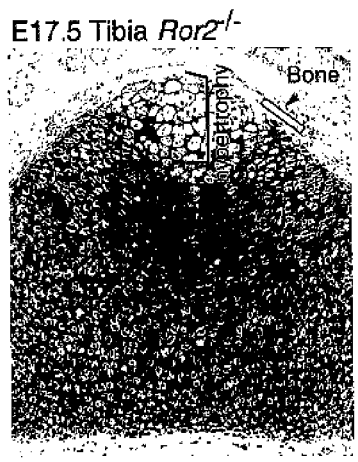

METHODS OF STIMULATING CARTILAGE FORMATION

This application claims priority to International Patent Application PCT/US01/05473, filed Feb. 20, 2001, which claims priority to U.S. Provisional Application 60/189,216, filed Mar. 14, 2000.

Throughout this application various publications are referenced. The disclosures of these publications in their entireties are hereby incorporated by reference into this application.

INTRODUCTION

The field of this invention is methods of stimulating cartilage formation and methods of use. In particular, cartilage formation is stimulated by stimulating chondrocyte growth, development and activity. The present invention also provides for novel assay systems useful for identifying novel ligands capable of stimulating chondrocyte growth, development and activity.

BACKGROUND OF THE INVENTION

Osteoarthritis, also known as degenerative joint disease, is the most common form of arthritis. In addition to man, nearly all vertebrates suffer from osteoarthritis. Osteoarthritis is characterized by damage to and subsequent loss of cartilage in the joints. Cartilage, a slippery connective tissue that is located on the articular surfaces of bones, is necessary for flexibility, support and protection of the bone. When cartilage is damaged due to, for example, injury or stress related to obesity, the joint can no longer function properly and painlessly. When the cartilage deteriorates, osteoarthritis develops.

Early in the progression of the disease, the surface of the cartilage swells and there is a loss of various tissue components, notably proteoglycans. Subsequently, fissures and pits appear on the cartilage and inflammation often occurs around the synovium. As the disease progresses further, the cartilage loses elasticity and becomes more and more susceptible to damage due to continued use and injury. Eventually, much of the cartilage is destroyed, resulting in unprotected bone surface, a condition which is extremely painful.

In an effort to repair the damage, the body often forms fluid-filled cysts around the bony areas or in the regions around the fissures. Local bone cells may respond to the damage by forming dense, misshapen plates around damaged and exposed areas, further limiting joint mobility.

Symptoms of osteoarthritis include pain, stiffness and loss of mobility in one or more joints. Severity of symptoms waxes and wanes with changing weather conditions, advancing disease, and following periods of inactivity.

Osteoarthritis is quite prevalent in the adult population, with over 85% of people over age 65 showing some evidence of the disease upon x-ray. Of these 35%–50% experience symptoms. The causes of osteoarthritis are $_1$ not completely known, but clearly age, genetic factors, muscle disuse and weakness, trauma, obesity and anatomical abnormalities contribute to the development of the disease. Prevention has focused on weight loss, exercise, hormone therapy such as estrogen replacement in postmenopausal women, and diet supplements such as vitamin D and calcium.

Current treatments are directed primarily towards alleviating symptoms (acetaminophen and non-steroidal anti-inflammatory drugs (NSAIDs) for pain, hyaluronic acid and exercise to help lubricate the joints, and steroids for inflammation). Surgical alternatives include arthroscopy, resection arthroplasty, osteotomy, chondroplasty and joint replacement.

Clearly, therapies are needed that are less invasive and expensive than surgery and that are directed to correcting the cause—degenerating cartilage, rather than treating a symptom such as pain or inflammation. In accordance with the present invention, Applicants have discovered that a previously described orphan receptor termed ROR2 (see U.S. Pat. No. 5,843,749) appears to play a critical role in cartilage formation and as such may be useful is developing therapeutic strategies to treat diseases of cartilage such as osteoarthritis.

REFERENCES

1. Barbacid, M. Neurotrophic factors and their receptors. *Curr Opin Cell Biol* 7, 148–155 (1995).
2. Dumont, D. J. et al. Dominant-negative and targeted null mutations in the endothelial receptor tyrosine kinase, tek, reveal a critical role in vasculogenesis of the embryo. *Genes & Development* 8, 1897–1909 (1994).
3. Sato, T. N. et al. Distinct roles of the receptor tyrosine kinases Tie-1 and Tie-2 in blood vessel formation. *Nature* 376, 70–74 (1995).
4. Davis, S. et al. Isolation of angiopoietin-1, a ligand for the TIE2 receptor, by secretion-trap expression cloning [see comments]. *Cell* 87, 1161–1169 (1996).
5. Suri, C. et al. Requisite role of angiopoietin-1, a ligand for the TIE2' receptor, during embryonic angiogenesis [see comments]. *Cell* 87, 1171–1180 (1996).
6. Maisonpierre, P. C. et al. Angiopoietin-2, a natural antagonist for Tie2 that disrupts in vivo angiogenesis [see comments]. *Science* 277, 55–60 (1997).
7. Ferrara, N. Vascular endothelial growth factor: molecular and biological aspects. *Curr Top Microbiol Immunol* 237, 1–30 (1999).
8. Eriksson, U. & Alitalo, K. Structure, expression and receptor-binding properties of novel vascular endothelial growth factors. *Curr Top Microbiol Immunol* 237, 41–57 (1999).
9. Valenzuela, D. M. et al. Receptor tyrosine kinase specific for the skeletal muscle lineage: expression in embryonic muscle, at the neuromuscular junction, and after injury. *Neuron* 15, 573–584 (1995).
10. DeChiara, T. M. et al. The receptor tyrosine kinase MuSK is required for neuromuscular junction formation in vivo. *Cell* 85, 501–512 (1996).
11. Glass, D. J. et al. Agrin acts via a MuSK receptor complex. *Cell* 85, 513–523 (1996).
12. Masiakowski, P. & Carroll, R. D. A novel family of cell surface receptors with tyrosine kinase-like domain. *J Biol Chem* 267, 26181–26190 (1992).
13. Oldridge, M. et al. Localized mutations within ROR2 (NTRKR2), an orphan receptor tyrosine kinase, cause brachydactyly type B. *Nature Genetics* submitted.
14. Davis, A. P., Witte, D. P., Hsieh-Li, H. M., Potter, S. S. & Capecchi, M. R. Absence of radius and ulna in mice lacking hoxa-11 and hoxd-11. *Nature* 375, 791–795 (1995).
15. ten Berge, D., Brouwer, A., Korving, J., Martin, J. F. & Meijlink, F. Prx1 and Prx2 in skeletogenesis: roles in the craniofacial region, inner ear and limbs. *Development* 125, 3831–3842 (1998).
16. Karaplis, A. C. et al. Lethal skeletal dysplasia from targeted disruption of the parathyroid hormone-related peptide gene. *Genes Dev* 8, 277–289 (1994).

17. Lanske, B. et al. PTH/PTHrP receptor in early development and Indian hedgehog-regulated bone growth [see comments]. *Science* 273, 663–666 (1996).
18. Vortkamp, A. et al. Regulation of rate of cartilage differentiation by Indian hedgehog and PTH-related protein [see comments]. *Science* 273, 613–622 (1996).
19. Weir, E. C. et al. Targeted overexpression of parathyroid hormone-related peptide in chondrocytes causes chondrodysplasia and delayed endochondral bone formation. *Proc Natl Acad Sci USA* 93, 10240–10245 (1996).
20. Schipani, E. et al. Targeted expression of constitutively active receptors for parathyroid hormone and parathyroid hormone-related peptide delays endochondral bone formation and rescues mice that lack parathyroid hormone-related peptide. *Proc Natl Acad Sci USA* 94, 13689–13694 (1997).
21. Muenke, M. & Schell, U. Fibroblast-growth-factor receptor mutations in human skeletal disorders. *Trends Genet* 11, 308–313 (1995).
22. Wilkie, A. O., Morriss-Kay, G. M., Jones, E. Y. & Heath, J. K. Functions of fibroblast growth factors and their receptors. *Curr Biol* 5, 500–507 (1995).
23. Deng, C., Wynshaw-Boris, A., Zhou, F., Kuo, A. & Leder, P. Fibroblast growth factor receptor 3 is a negative regulator of bone growth. *Cell* 84, 911–921 (1996).
24. Colvin, J. S., Bohne, B. A., Harding, G. W., McEwen, D. G. & Ornitz, D. M. Skeletal overgrowth and deafness in mice lacking fibroblast growth factor receptor 3. *Nat Genet* 12, 390–397 (1996).
25. Naski, M. C., Colvin, J. S., Coffin, J. D. & Ornitz, D. M. Repression of hedgehog signaling and BMP4 expression in growth plate cartilage by fibroblast growth factor receptor 3. *Development* 125, 4977–4988 (1998).
26. DeChiara, T. M. et al. Mice lacking the CNTF Receptor, unlike mice lacking CNTF, exhibit profound motor neuron deficits at birth. *Cell* 83, 313–322 (1995).
27. Conover, J. C. et al. Neuronal deficits, not involving motor neurons, in mice lacking BDNF and/or NT4. *Nature* 375, 235–238 (1995).
28. McLeod, M. J. Differential staining of cartilage and bone in whole mouse fetuses by alcian blue and alizaren red S. *Teratology* 22, 299–301 (1980).
29. Mercer, E. H., Hoyle, G. W., Kapur, R. P., Brinster, R. & Palmiter, R. D. The dopamine b-hydroxylase gene promoter directs expression of *E. coli* lacZ to sympathetic and other neurons in adult transgenic mice. *Neuron* 7, 703–716 (1991).
30. Vanky, P., Brockstedt, U., Hjerpe, A. & Wikstrom, B. Kinetic studies on epiphyseal growth cartilage in the normal mouse. *Bone* 22, 331–339 (1998).

SUMMARY OF THE INVENTION

Receptor tyrosine kinases often play critical roles for particular cell lineages by initiating important signaling cascades in those lineages. Examples include the neural-specific Trk receptors[1], the VEGF and Angiopoietin endothelial-specific receptors[2-8], and the muscle-specific MuSK receptor[9-11]. Many lineage-restricted receptor tyrosine kinases were initially identified as "orphans" homologous to known receptors, and only subsequently used to identify their unknown growth factors. There are few remaining receptor tyrosine kinase-like orphans still lacking identified ligands as well as clear-cut biological roles. Applicants describe herein a detailed characterization of one such orphan, termed ROR2[12], whose activation may play a role in treating diseases such as osteoarthritis which are characterized by destruction and loss of cartilage.

In the present application, Applicants disclose that ROR2 drives chondrocyte growth, development and activity. Because of this, Applicants contend that activating ROR2 may be useful in treating diseases and disorders wherein cartilage is damaged or destroyed. Stimulation of the growth, development and activity of chondrocytes would result in formation of new cartilage or repair of damaged cartilage.

Therefore, one embodiment of the invention is a-method of increasing chondrocyte growth, development and activity comprising contacting chondrocytes expressing a ROR2 receptor with an agent capable of activating the ROR2 receptor.

Another embodiment of the invention is a method of increasing cartilage formation comprising contacting chondrocytes expressing a ROR2 receptor with an agent capable of stimulating chondrocyte growth, development and activity.

A preferred embodiment of the invention is a method of treating a patient with damaged or diseased cartilage comprising administering to the patient an agent capable of activating a ROR2 receptor.

Another embodiment of the invention is the method of increasing chondrocyte growth, development and activity comprising contacting chondrocytes expressing a ROR2 receptor with an agent capable of activating the ROR2 receptor, the method of treating a patient with damaged or diseased cartilage comprising administering to the patient an agent capable of activating a ROR2 receptor, or the method of treating a patient with damaged or diseased cartilage comprising administering to the patient an agent capable of activating a ROR2 receptor wherein the agent is an activating antibody.

In a further embodiment of the invention the method of increasing chondrocyte growth, development and activity comprising contacting chondrocytes expressing a ROR2 receptor with an agent capable of activating the ROR2 receptor, the method of treating a patient with damaged or diseased cartilage comprising administering to the patient an agent capable of activating a ROR2 receptor, or the method of treating a patient with damaged or diseased cartilage comprising administering to the patient an agent capable of activating a ROR2 receptor is where the agent is a monoclonal antibody, a wholly human monoclonal antibody, a ligand of the ROR2 receptor, a naturally occurring ligand of the ROR2 receptor, or a small molecule.

A preferred embodiment of the invention is a method of identifying an agent capable of activating the ROR2 receptor comprising (a) obtaining cells expressing the ROR2 receptor; (b) subjecting the cells to a test agent; (c) determining whether the test agent has activated the ROR2 receptor. In yet another preferred embodiment of the invention the cells are obtained from an animal, are chondrocytes or are obtained by transfecting cells that normally do not express the ROR2 receptor with the ROR2 receptor nucleic acid under conditions in which the cell expresses the ROR2 receptor protein on the cell surface.

A further embodiment of the invention involves determining whether the ROR2 receptor has been activated by measuring phosphorylation of the receptor or by measuring chondrocyte growth, development or activity.

In another embodiment of the invention, the ROR2 receptor is used in assays designed to identify natural ligands of the receptor or small molecules or antibodies capable of activating the receptor and stimulating chondrocyte growth, development and activity.

A preferred embodiment of the invention is a method of preventing chondrocyte growth, development and activity comprising contacting chondrocytes expressing a ROR2 receptor with an agent capable of blocking activation of the ROR2 receptor.

Another embodiment of the invention is a method of preventing cartilage formation comprising contacting chondrocytes expressing a ROR2 receptor with an agent capable of preventing chondrocyte growth, development and activity by binding to but not activating the ROR2 receptor wherein the agent is a neutralizing antibody, a monoclonal antibody, a wholly human monoclonal antibody or wherein the agent is a ligand of the ROR2 receptor including a naturally occurring ligand of the ROR2 receptor. Also contemplated in an embodiment wherein the agent is a small molecule.

A further embodiment is a method of identifying an agent capable of blocking activation of the ROR2 receptor comprising (a) obtaining cells expressing the ROR2 receptor; (b) subjecting the cells to a test agent; (c) determining whether the test agent has blocked activation of the ROR2 receptor. In one embodiment of the invention, the cells are obtained from an animal and in another embodiment, the cells are chondrocytes. In a preferred embodiment of the invention, the cells are obtained by transfecting cells that normally do not express the ROR2 receptor with the ROR2 receptor nucleic acid under conditions in which the cell subsequently expresses the ROR2 receptor protein on the cell surface.

In one preferred embodiment of the invention, the method of determining whether the ROR2 receptor activation has been blocked is accomplished by measuring phosphorylation of the receptor and in another preferred embodiment, the method of determining whether the ROR2 receptor activation has been blocked is accomplished by measuring chondrocyte growth, development or activity.

A further preferred embodiment of the invention is an agent identified by any of the above-described methods.

As stated supra, the present invention also provides for antibodies to the ROR2 receptor. For preparation of monoclonal antibodies directed toward ROR2 receptor, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy", Alan R. Liss, Inc. pp. 77–96) and the like are within the scope of the present invention.

The monoclonal antibodies for diagnostic or therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to the ROR2 receptor described herein. For the production of antibody, various host animals can be immunized by injection with the ROR2 receptor, or fragments or derivatives thereof, including but not limited to rabbits, mice and rats. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected ROR2 receptor epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include, but are not limited to, the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques including, but not limited to, immunoabsorption or immunoaffinity chromatography, chromatographic methods such as HPLC (high performance liquid chromatography), or a combination thereof. Wholly human monoclonal antibodies are also provided for and can be made as described in U.S. Pat. No. 5,939,598, issued Aug. 17, 1999 and assigned to Abgenix, Inc.

DETAILED DESCRIPTION OF THE INVENTION

Disruption of the murine ROR2 gene leads to profound skeletal abnormalities, with essentially all endochondrally derived bones foreshortened and/or misshapen, albeit to differing degrees. ROR2 is selectively expressed in the chondrocytes of all developing cartilage anlagen, where it plays a critical role during initial growth and patterning, as well as subsequently in the proliferating chondrocytes of mature growth plates, where it is required for normal expansion. These findings led to the realization that mutations in ROR2 cause inherited limb malformations in man[13].

Figure 1A:
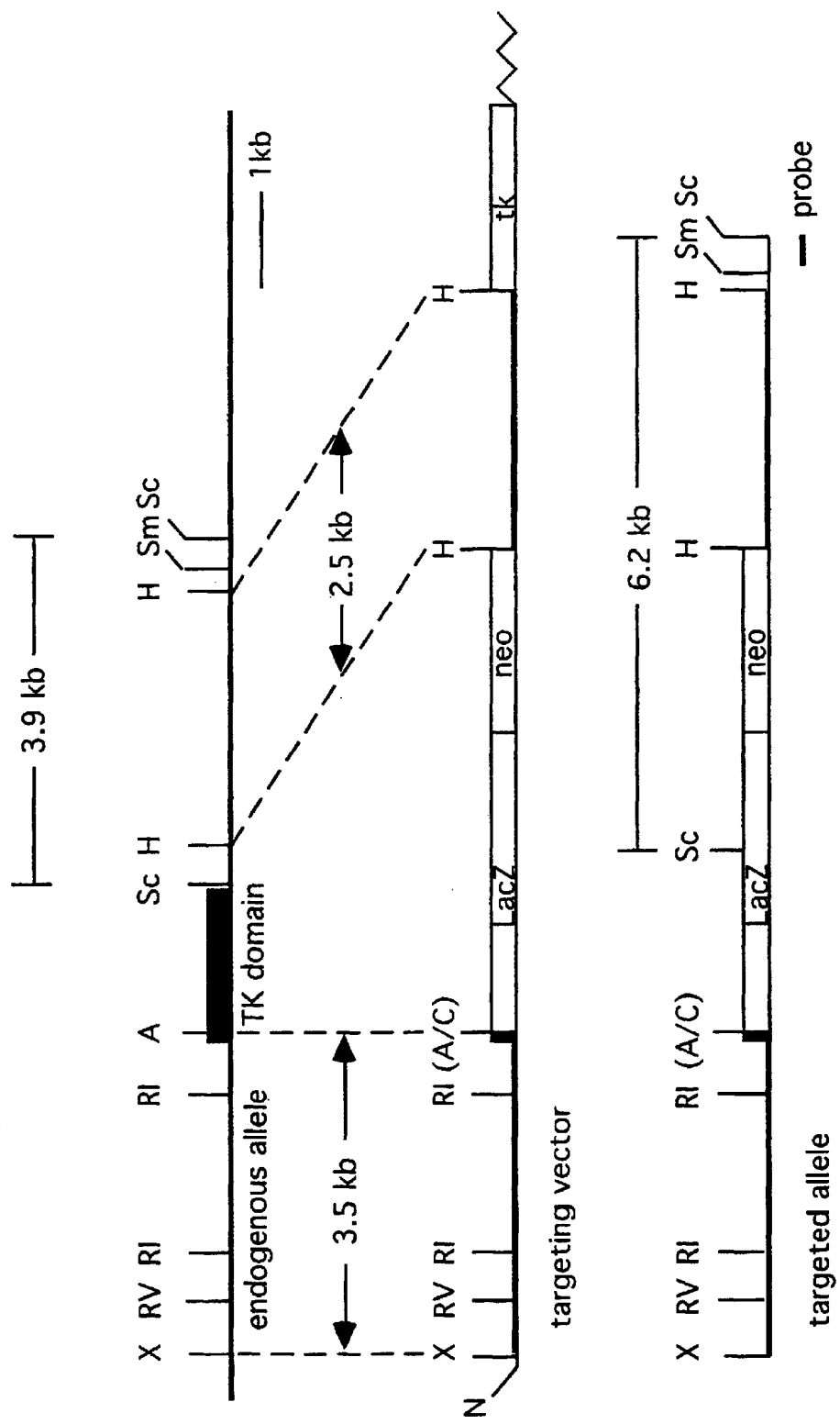
FIG. 1. Disruption of the endogenous murine ROR2 allele, resulting in the encoding of a novel product in which the ecto- and transmembrane-domains of ROR2 are fused to LacZ (which replaces the normal tyrosine kinase-like cytodomain). a, Top schematic depicts the murine genomic region spanning the exon encoding the entire tyrosine kinase-like domain of ROR2, as well as the following ST1/PR/ST2 motifs (exon in black and designated "TK domain"). Middle schematic shows the targeting vector, with the indicated regions of homology to the above endogenous allele; "LacZ" signifies the beta galactosidase coding region which was fused in frame to the beginning of the TK domain, "neo" signifies the subsequent neo resistance gene used for positive selection, and "tk" signifies the herpes virus thymidine kinase gene used for negative selection. Lower schematic represents the predicted disrupted allele after targeting. X, Xba1; RV, EcORV; RI, EcOR1; A, AccI; C, ClaI; Sc, SacI; H, HindIII; Sm, Sma1. b, Schematic depicting how the LacZ allele was fused in frame to the ROR2 coding region, just after the transmembrane domain; the usual initiating methionine used by LacZ is indicated (see Methods). c, Southern analysis depicting genomic analysis which distinguishes ROR2+/+mice, ROR2+/−mice, and ROR2−/− mice; tail DNA from these mice was digested with Sac1 and probed with the fragment indicated at bottom right of panel A, which detects a 3.9 kb Sac1 fragment from the normal allele but a 6.2 kb fragment from the disrupted allele (see panel A). d, Northern analysis demonstrating loss of endogenous ROR2 transcript in total E15.5 limb RNA prepared from ROR2−/− mice; embryonic RNA from both ROR2+/−mice and ROR2−/− mice express a novel ROR2/ LacZ chimeric transcript, hybridizing with both a ROR2 ectodomain probe (shown) and a LacZ probe (not shown) but not a kinase domain probe (shown), as expected.
Figure 1B:
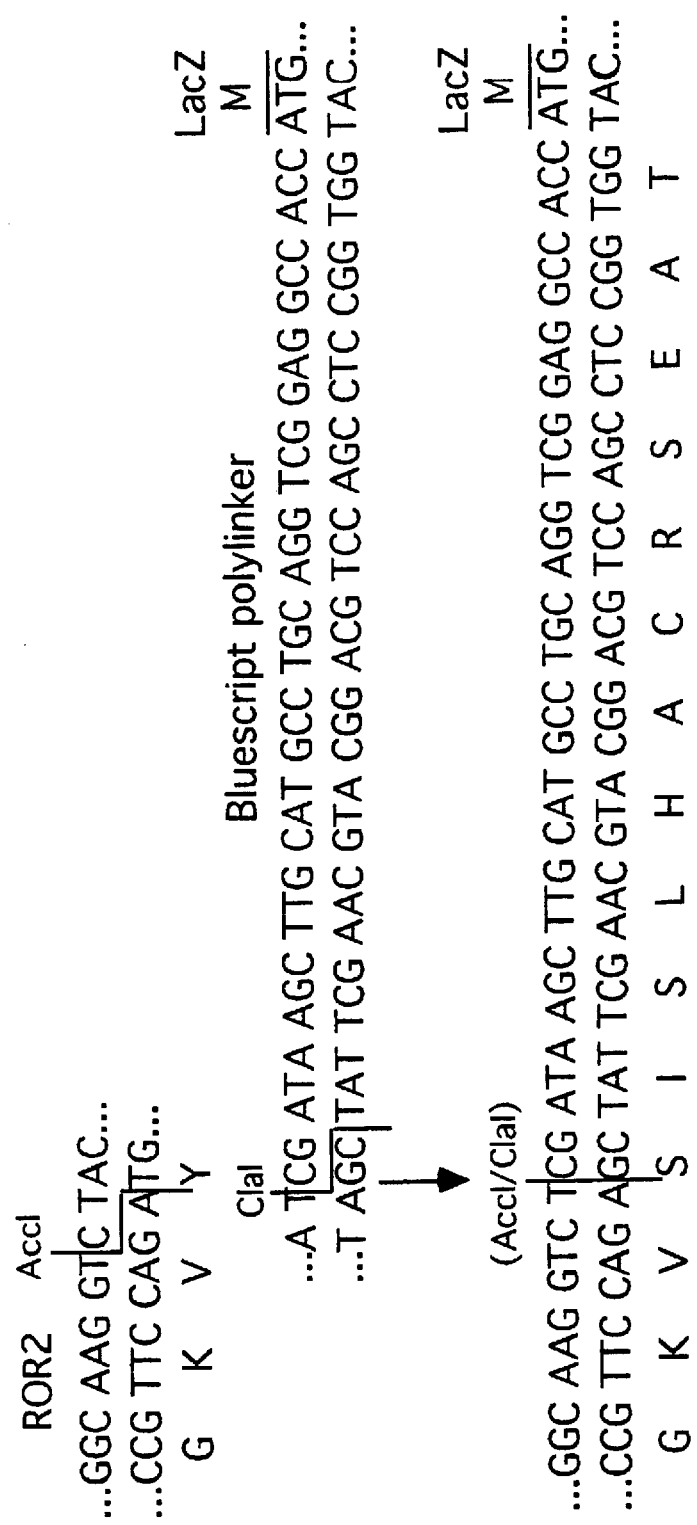
Figure 1C:
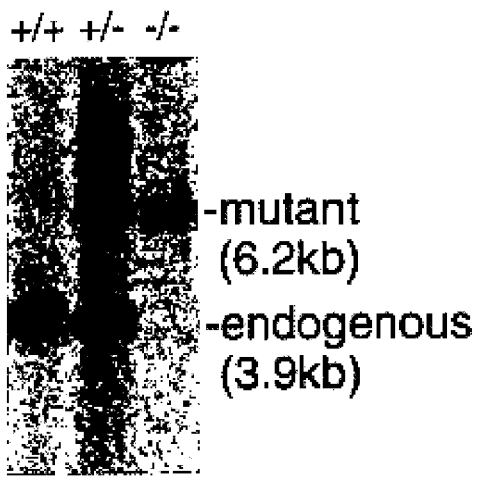
Figure 1D:
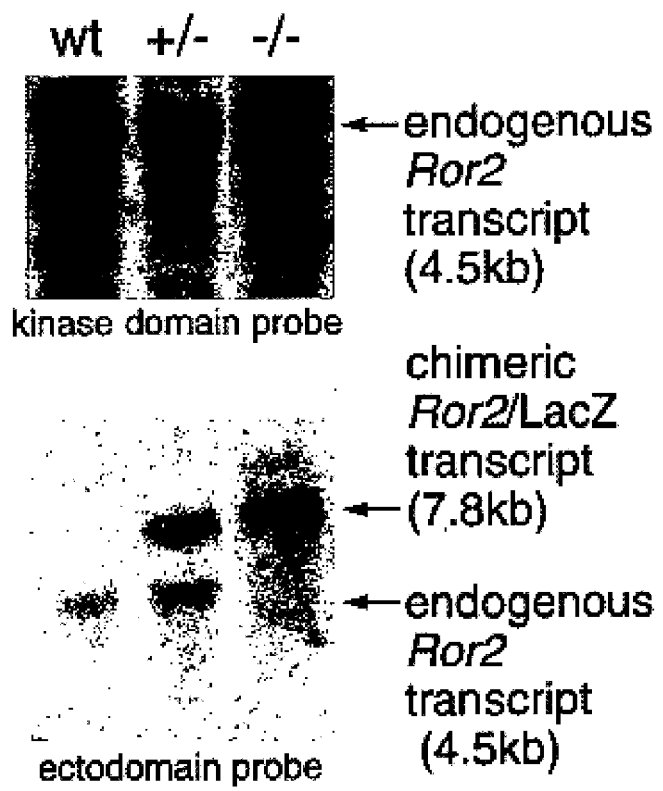
Figure 2A:
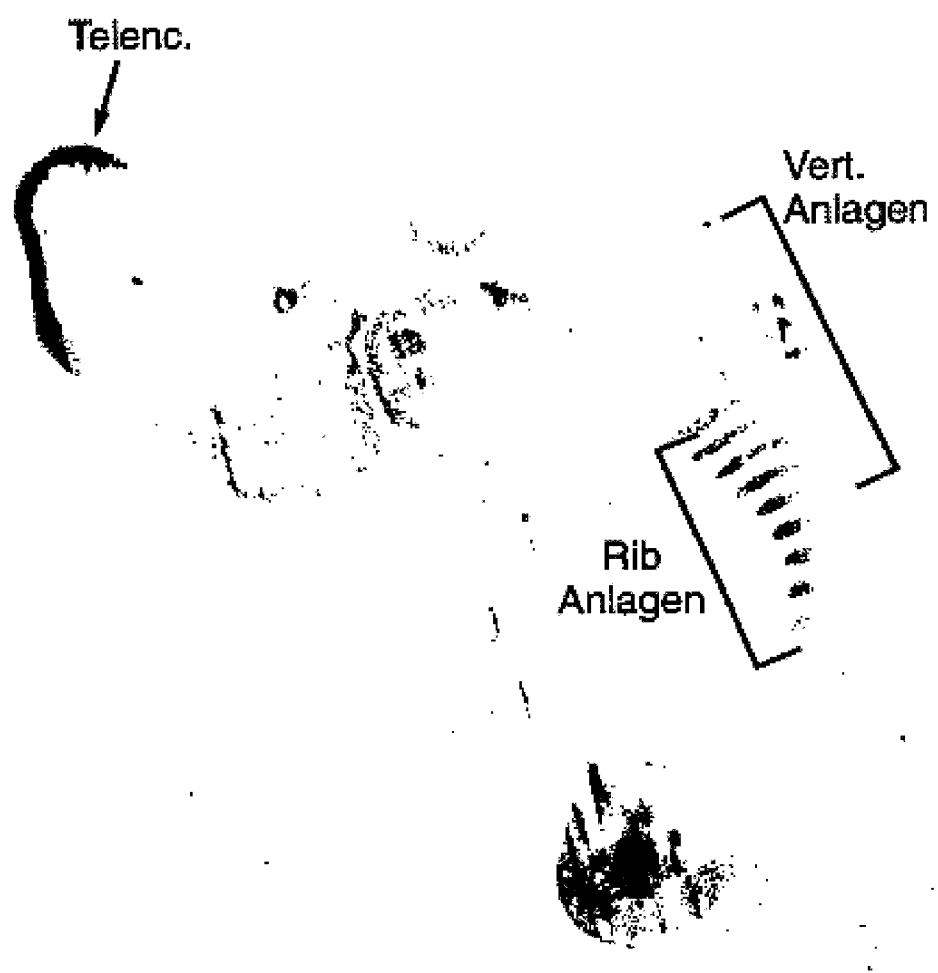
FIG. 2. ROR2 is expressed in chondrocytes of early cartilaginous anlagen in embryos, as well as in chondrocytes of articular cartilage and growth plates in the adult. a, In sagittal section of entire E12 ROR2+/−embryo, ROR2 expression (visualized by LacZ staining) is notable in developing rib and vertebral anlagen, though also noted in telencephalic neuroepithelium of forebrain and snout region; surrounding mesenchyme and stroma are largely negative. b, High-power view of ROR2 staining (visualized by LacZ staining) in rib anlagen from embryo shown in previous panel, showing lack of expression in surrounding mesenchyme and stroma. c, ROR2 expression (visualized by LacZ staining) in developing limb at E13; note that all cartilaginous anlagen of developing limb bones which appear in section are stained, as is perichondrium and dermis; note that surrounding mesenchyme and stroma are largely negative. d1 & d2, In situ hybridizations of E13 rib anlagen and limb, confirming that LacZ staining in previous panels reflects mRNA expression patterns. e, Low-power view of section through adult femur of ROR2+/−mouse, revealing specific ROR2 expression (visualized by LacZ staining) in articular cartilage, growth plate, and perichondrial/periosteal region. f, Higher-power view of section shown from previous panel. g, Histologic section of a femur from a post-natal day 3 (P3) ROR2+/−pup stained for LacZ, revealing specific expression in reserve and proliferative zones of growth plate, as well as in perichondrium, but not in hypertrophic zone.

Applicants genetically engineered a ROR2 allele in mice in which the ROR2 kinase-like domain was replaced by the beta-galactosidase (LacZ) coding region, allowing for simultaneously knocking out ROR2 function and performing LacZ staining to follow ROR2 expression patterns (FIGS. 1a,b). Mice heterozygous for the mutant allele (ROR2+/−, FIGS. 1c,d) were viable, fertile and appeared normal. Expression analysis in heterozygous embryos, visualized using the LacZ reporter, revealed that ROR2 was selectively expressed in the chondrocytes of the developing anlagen of all bones forming by endochondral ossification, such as those for the rib and limb bones; staining was also noted in the perichondrial region and dermis, though surrounding mesenchyme and stroma were largely negative (FIGS. 2b,c); in situ hybridization analyses confirmed that LacZ staining reflected endogenous ROR2 mRNA expression patterns (FIGS. 2d1,d2). ROR2 expression was noted in limited other sites (such as telencephalon and dermis in the snout region, FIG. 2a). Notably, ROR2 expression was not observed in precursor regions of bones forming without a cartilaginous anlage, such as the frontal and parietal bones of the skull that form by intramembranous ossification (FIG. 2a).

Consistent with the notion that ROR2 continues to play a key role in chondrocytes later in development, ROR2 is expressed post-natally in articular cartilage, perichondrium (as well as periosteum), and a particular subset of growth plate chondrocytes—reserve and proliferating but not hypertrophic chondrocytes (FIGS. 2e,f,g); ROR2 was absent in bone tissue itself.

Figure 3A:
FIG. 3. Disruption of murine ROR2 allele results in widespread skeletal abnormalities (in bones formed by endochondral but not intramembranous ossification), though distal long bones in limb are more dramatically affected than proximal long bones. a, Wild-type pup compared to ROR2−/− littermate shortly after birth. b, Comparison of newborn pups after staining with alcian blue and alizarin red S to visualize the cartilaginous (in blue) and ossified (in red) portions of their skeletons; inset shows normal appearance in ROR2−/− embryos of frontal (F) and parietal (P) skull bones forming by intramembranous ossification. c and d, Close-up views of forelimbs from skeletons depicted in previous panel, showing more dramatic abnormalities in distal long bones (radius and ulna) as compared to proximal long bone (humerus); arrowheads point to ossification centers of proximal (P), middle (M) and distal (D)phalanges, highlighting the missing middle (M) phalanges in ROR2−/− embryos. e, Length dimensions of proximal and distal long bones of the limbs in ROR2−/− embryos and newborns, presented as % decrease from their wild-type littermate counterparts; though all bones are shortened in the ROR2−/− mice, note that the distal long bones (radius and tibia) are much more dramatically shortened than the proximal long bones (humerus and femur).
Figure 3B:
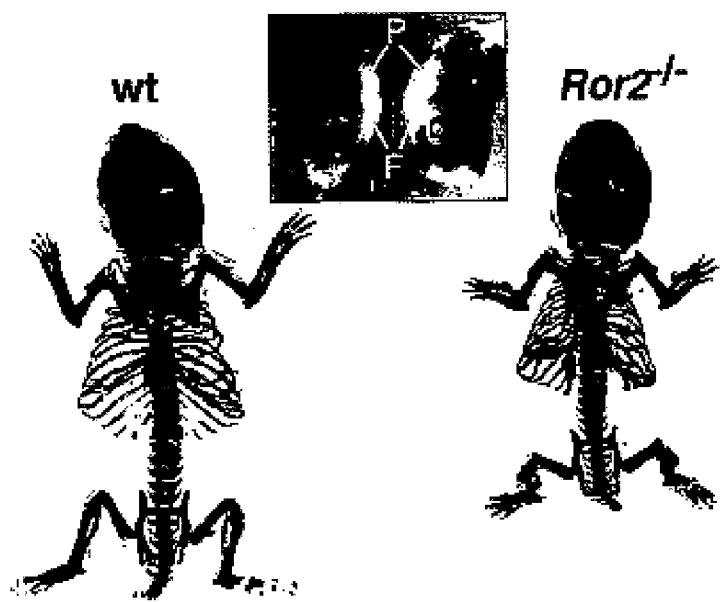

Confirmation that ROR2 expression patterns underlie a critical and specific role for ROR2 during cartilage development came from the generation of mice homozygous for the ROR2 mutant allele (ROR2−/− mice, FIGS. 1c,d), which exhibited perinatal lethality, with shortened snout, limbs and tail as well as cleft palate (FIG. 3a). Newborn pups were stained with alizarin red S and alcian blue to visualize the cartilaginous (in blue) and ossified (in red) portions of their skeletons, revealing widespread abnormalities (FIG. 3b).

Figure 3C:
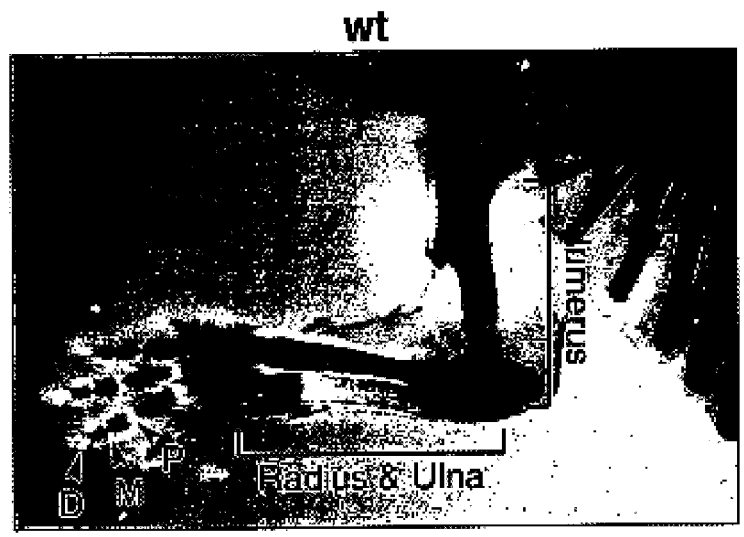
Figure 3D:

While skull bones formed by intramembranous ossification were apparently unaffected in ROR2−/− mice (FIG. 3b, inset), essentially all bones formed by endochondral ossification were foreshortened and misshapen, albeit to differing degrees, with a tendency toward greater abnormalities more distally. For example, while the proximal long bones in both the forelimb and hindlimb (i.e., the humerus and femur) were only subtly abnormal in shape (FIGS. 3c,d) and only moderately shorter in the ROR2−/− littermates (by 10–20% versus controls, FIG. 3e), the distal long bones in the limbs (i.e., the radius and ulna in the forelimb, and the tibia and fibula in the hindlimb) were much more obviously deformed (FIGS. 3c,d and see below) and much shorter in length (by 50–60% versus controls, FIG. 3e). The digits were not only shortened in the ROR2−/− pups, but missing the middle phalanges (FIGS. 3c,d). The lumbar vertebrae of ROR2−/− mice were not grossly misshapen, but were quantitatively smaller in both length and width, while the more distal coccygeal vertebrae were grossly misshapen and greatly reduced in size (FIG. 3b). Altogether, ROR2 expression patterns together with the severe skeletal abnormalities in ROR2−/− mice indicate that ROR2 plays a direct and required role in endochondral bone formation; preliminary examination failed to reveal obvious defects in other tissues.

Figure 4A:
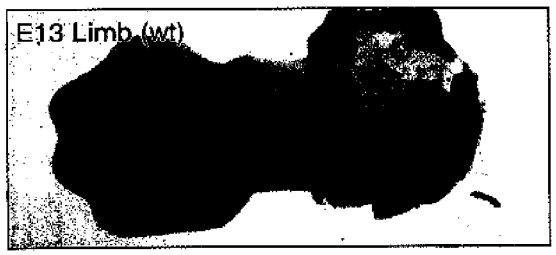
FIG. 4. Developmental progression of abnormalities in cartilaginous anlagen of ROR2−/− mice. a–d, Alcian blue stains of whole limbs from E13 and E14 embryos reveal that cartilaginous anlagen in ROR2−/− embryos are shorter than their wild-type littermates, but not obviously abnormal in shape at these early stages except for the missing anlagen for the middle phalanges (indicated by arrow in wild-type paw in panel c). e–h, at slightly later stages, limb sections shown at the same magnification reveal that ROR2−/− anlagen are not only dramatically shorter, but obviously abnormal in shape; notably, instead of developing a central ossified region flanked by symmetric hypertrophic zones and growth plates as do the wild-type littermates, the ROR2−/− mice develop a delayed and eccentric hypertrophic region that juts out from the side of the developing anlage, covered by an abnormally positioned thin collar of bone. i–k, higher-power views focusing on progression of abnormal eccentric hypertrophic region, and associated abnormal peripheral ossification that forms the bony collar, in developing bones from E15.5 to E17.5 ROR2−/− embryos. l–m, Comparison of distal long bones from hindlimbs of E17.5 ROR2−/− embryos with those of their wild-type littermates, showing how eccentric hypertrophic region detailed above seems to result in grossly abnormal appearance of these bones, creating progressive bends in the bone.
Figure 4B:
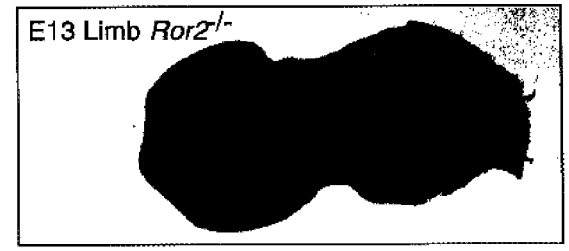
Figure 4C:
Figure 4D:
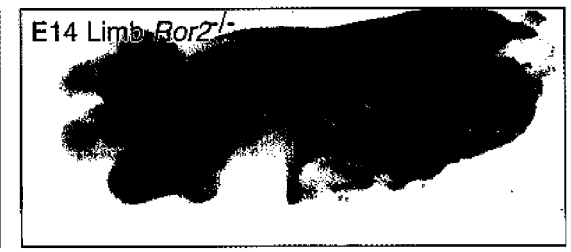
Figure 4E:
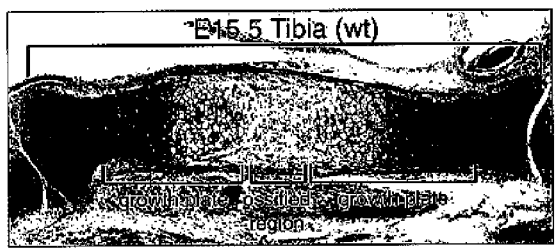
Figure 4F:
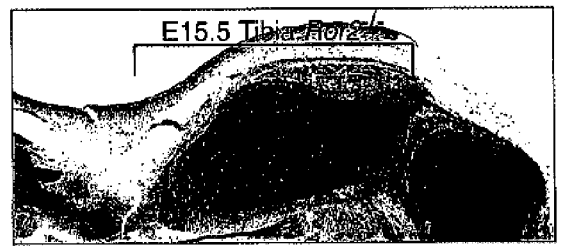
Figure 4G:
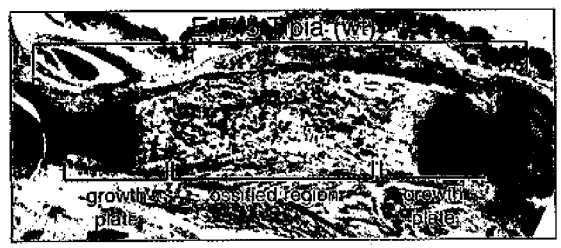
Figure 4H:
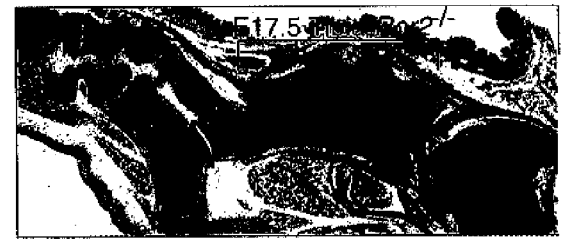
Figure 4L:
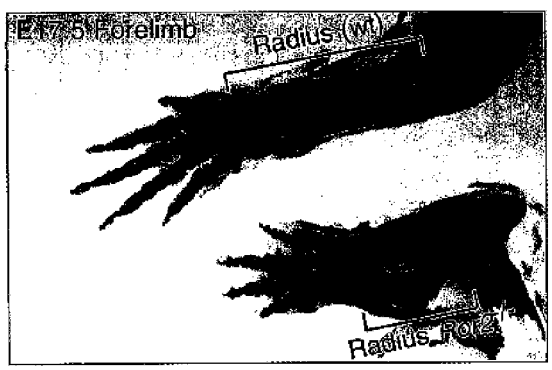
Figure 4M:
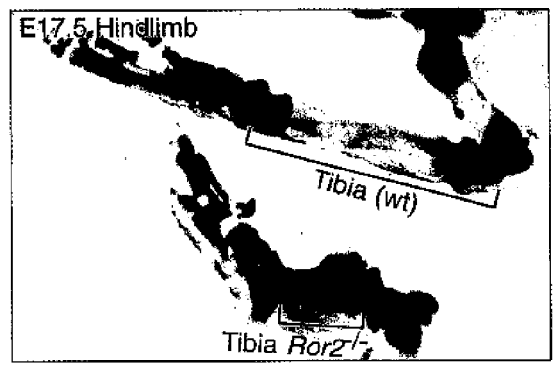

Abnormalities in cartilage anlagen of ROR2−/− embryos were seen shortly after their formation. At embryonic day 13 (E13) and E14, the anlagen in the limbs were notably shorter than normal, though not dramatically abnormal in shape (FIGS. 4a-d) except for missing the anlagen for middle phalanges (arrow, FIGS. 4c,d). One day later in development, the distal limb anlagen were not only shorter, but obviously abnormal in shape, with delayed hypertrophication and ossification (FIGS. 4e,f). Instead of forming a central hypertrophic zone divided by a central ossified region resulting in two flanking growth plates (FIGS. 4e,g), ROR2−/− anlagen displayed delayed eccentric hypertrophy covered by a bony collar, forming a characteristic abnormal knob on one side of the developing bone (FIGS. 4f,h,i-k and 5a), and apparently leading to the gross abnormalities eventually noted in the older limb bones (FIGS. 4l,m). The initially shortened limb anlagen in ROR2−/− embryos suggest that ROR2 is required for proper growth, development and activity of chondrocytes normally expressing this receptor, while the subsequent gross abnormalities in anlage and growth plate organization suggest that ROR2 function is required for proper patterning of developing anlagen.

Figure 5A:
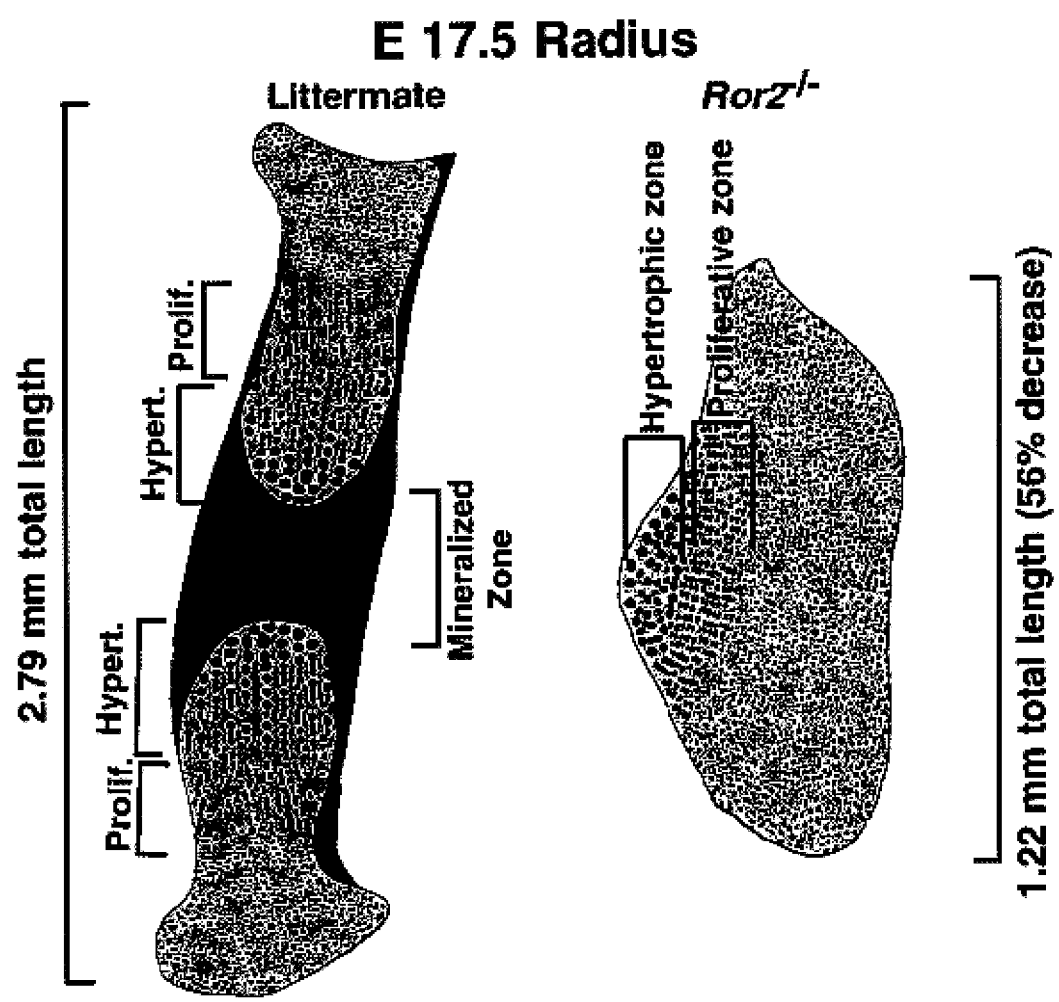
FIG. 5. Schematic summary of comparison between forelimb long bones in normal and ROR2−/− embryos at E17.5. a, The E17.5 radius shows a profound decrease of 56% in the length of the bone, as well as an abnormal eccentric orientation of the proliferative and hypertrophic zones in the ROR2−/− bone compared with the proximo-distal orientation of these zones in the normal radius. b, Summary of E17.5 humerus data showing the decrease in the width of the proliferative zones and the increase in the width of the hypertrophic zones in both the proximal and distal growth plates of the ROR2−/− embryo, with this abnormal interplay of these growth plate zones presumably leading to the overall reduction of 19.5% in total humerus bone length.
Figure 5B:
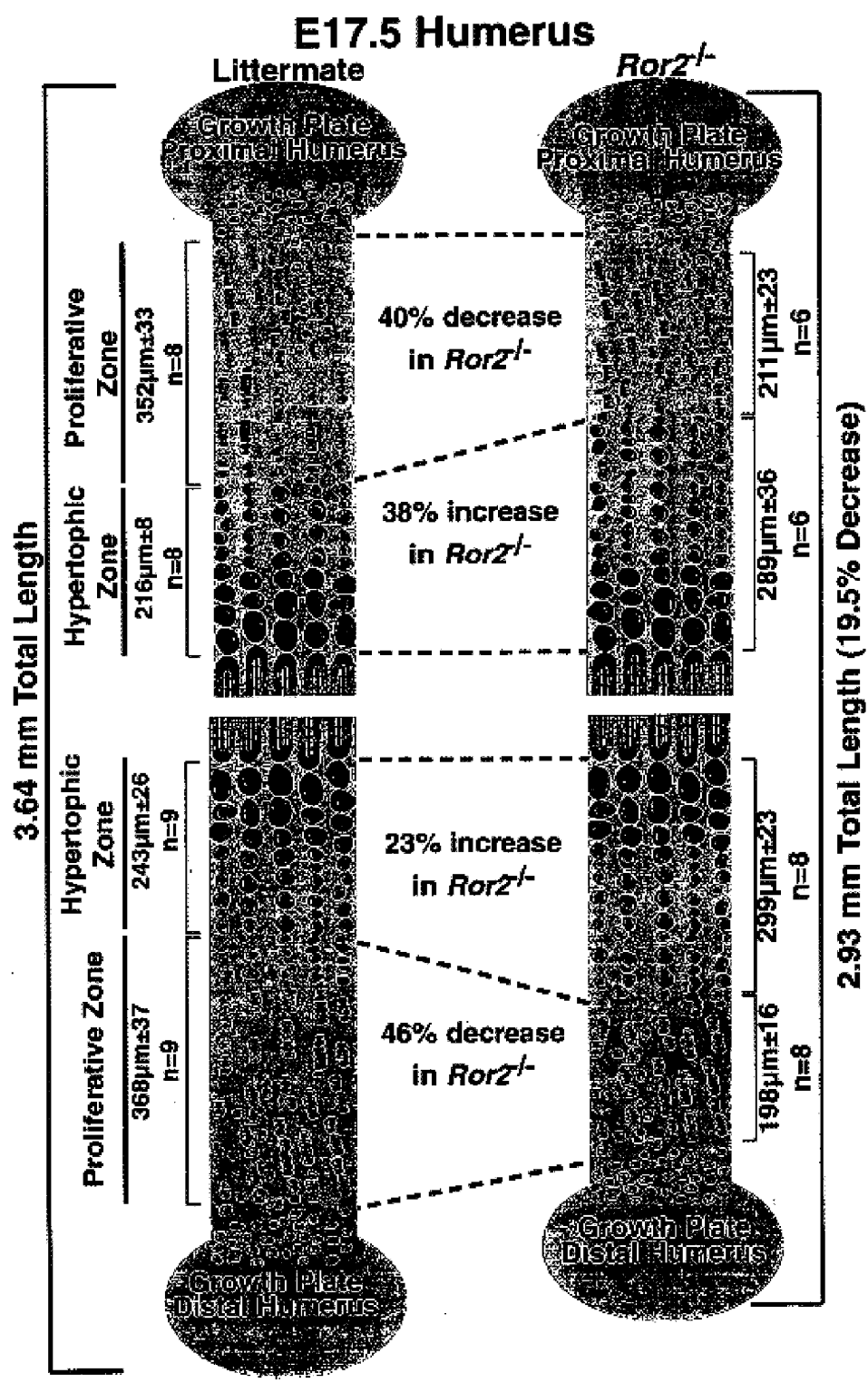

Consistent with the notion that ROR2 continues to play a critical role later during growth plate expansion, where it continues to be expressed in reserve and proliferating chondrocytes (see above), growth plate structure was markedly abnormal in later embryos, even in the more moderately affected proximal limb bones. Thus, proliferative zone width in these growth plates were reduced by almost half, while hypertrophic zone width increased by 2338% (FIG. 5b); these changes combined to yield shorter growth plates overall (FIG. 5b). Thus, the modest reductions in the length of proximal limb bones in ROR2−/− mice likely result from alterations in the normally coupled interplay between proliferative and hypertrophic zones.

Altogether, the above analyses indicate that ROR2 plays a profound role in the initial growth and patterning of developing cartilage anlagen and their growth plates, as noted in the more distal limb bones, and that it continues to be required for the normal interplay and expansion of proliferative and hypertrophic zones in maturing growth plates, as noted in proximal limb bones. Detailed characterization of ROR2 expression patterns is consistent with a direct role for ROR2 in regulating chondrocyte growth, development and activity, as ROR2 is selectively expressed in the chondrocytes of the early anlagen as well as in resting and proliferative (but not hypertrophic) chondrocytes in older growth plates. Confirming ROR2 as a fundamentally important player in skeletal development, ROR2 mutations have been shown as the cause of inherited limb malformations in man[13]. The phenotype in humans is substantially milder than in ROR2−/− mice, probably because the ROR2−/− mice are homozygous for mutations removing the entire ROR2 tyrosine kinase-like domain, while the human mutations are found in heterozygotes and appear to act as partial dominant negatives; retaining most of the ROR2 TK-like domains[13].

Remaining questions include the varying severity of the ROR2−/− phenotype in different bones, and the role of ROR2 in the context of all the other pathways acting to regulate cartilage growth, development and activity. The role of ROR2 in the more severely affected distal long bones, in which it is critical for initial growth and patterning of the anlage and its growth plates, appears to be unlike that proposed for any other secreted growth factor pathway. Interestingly, there is some similarity between the severe organizational defects observed in these distal limb bones of the ROR2−/− mice, and those previously noted in mice doubly mutant for the paralogous homeobox genes hoxa-11 and hoxd-11[14]; as well as in mice doubly mutant for two other homeobox genes, Prx1 and Prx2[15], suggesting that ROR2 may be involved in a novel pathway involving these homeobox genes. In the maturing growth plates of modestly affected bones, the role of ROR2 seems somewhat analogous to that of the Indian Hedgehog (Ihh)/parathyroid hormone-related peptide (PTHrP) loop, since disruption of either depletes the proliferative zone[16-20]. Conversely, ROR2 appears to oppose the actions of the FGFR3 pathway at the growth plate, since FGFR3 disruption leads to expansion of the proliferative zone[21-25]. Thus, the two receptor tyrosine kinases now known to be required for normal growth plate expansion may push chondrocytes in opposite directions, with ROR2 promoting chondrocyte growth, development and activity and FGFR3 limiting such growth, development and activity. Preliminary attempts to examine expression patterns of Ihh, PTHrP and other factors during the development of proximal long bones in ROR2−/− mice do not reveal obvious alterations. Though subtle differences cannot be excluded, these findings are consistent with the possibility that ROR2 initiates an entirely separate pathway.

Applicants findings indicate that ROR2 is especially important for the chondrocyte lineage. In addition to its expression by chondrocytes comprising cartilaginous anlagen and at the growth plate, ROR2 is also expressed by other chondrocytes in the adult, such as those in the articular cartilage surface of joints and the fibrocartilaginous menisci of the knee. Osteoarthritis results from damage to the articular surface in joints, coupled with the inability of this surface to regenerate. Since ROR2 apparently drives chondrocyte growth, development and activity, promoting ROR2 function could be of benefit in this and other clinical settings.

EXAMPLES

Example 1

Construction of Targeting Vector and ES Cell Manipulations

The ROR2 gene targeting vector was constructed from mouse genomic DNA fragments isolated from a lambda FIX II phage library prepared with 129 strain mouse DNA (Stratagene). The 3.5 kb XhoI-AccI fragment depicted in FIG. 1a is comprised mostly of intron sequence except for the 75 nucleotides of coding sequence that terminated in the AccI site. The AccI site was filled in using Klenow DNA Polymerase in the presence of dATP and dGTP and was blunt-end ligated to a promoter-less LacZ gene cassette[5] that possessed a short upstream bluescript polylinker sequence terminating in a 5' ClaI site that was similarly filled-in using dCTP and dGTP to created an in-frame fusion at the $25^{th}$ amino acid from the start of the tyrosine kinase domain of ROR2 with the LacZ coding region as shown in FIG. 1B. At the HindIII site located between the PGK-neo expression cassette and the HSV-tk expression cassette in the targeting vector a 2.5 kb HindIII fragment taken from a genomic DNA region 0.7 kb downstream from the end of the ROR2 tyrosine kinase exon (FIG. 1A) was inserted. The vector was linearized by digestion with NotI and electroporated into E14.1 embryonic stem (ES) cells to select for homologous recombinant clones as previously described[26,27]. Of 276 doubly selected ES clones, 3 were targeted and two of these were successfully passed through the germ-line of male chimeric mice, both yielding similar homozygous phenotypes. The genotyping of heterozygous and homozygous mice was achieved by Southern blotting analysis using a 350 bp SacI-Sma fragment (FIG. 1A).

Example 2

Alizarin Red S, Alcian Blue and LacZ Stainings

Embryos derived from crosses between ROR2+/−matings were subjected to skeletal stains to visualize cartilage and bone as described[28]. For LacZ staining, embryos were fixed in 4% paraformaldehyde for 12 hours (E12–15.5) or 24 hours (E17.5 and P1), frozen in OCT or embedded in paraffin (for bone morphology), sectioned and stained for LacZ as described[29], or stained with safranin O/fast green to visualize cartilage and bone.

Example 3

Quantitation of Bone Lengths and Growth Plate Zones

Bone lengths and various zones[30] in the growth plate were measured from histological sections using the OsteoMeasure morphometry system (OsteoMetrics Inc., Atlanta, Ga.)

Although the foregoing invention has been described in some detail by way of illustration and example, it will be readily apparent to those of ordinary skill in the art that certain changes and modifications may be made to the teachings of the invention without departing from the spirit or scope of the appended claims.

We claim:

1. A method of increasing chondrocyte growth, development and activity comprising contacting chondrocytes expressing a ROR2 receptor with an agent capable of activating the ROR2 receptor.

2. A method of increasing cartilage formation comprising contacting chondrocytes expressing a ROR2 receptor with an agent capable of stimulating chondrocyte growth, development and activity by binding to the ROR2 receptor.

3. A method of treating a patient with damaged or diseased cartilage:
   comprising administering to the patient an agent capable of activating a ROR2 receptor.

4. The method of claim 1, 2, or 3 wherein the agent is an activating antibody.

5. The method of claim 4 wherein the activating antibody is a monoclonal antibody.

6. The method of claim 5 wherein the monoclonal antibody is a wholly human monoclonal antibody.

7. The method of claims 1, 2, or 3 wherein the agent is a ligand of the ROR2 receptor.

8. The method of claims 7 wherein the ligand is a naturally occurring ligand of the ROR2 receptor.

9. The method of claim 1, 2 or 3 wherein the agent is a small molecule.

10. A method of identifying an agent capable of activating the ROR2 receptor comprising:
    (a) obtaining cells expressing the ROR2 receptor;
    (b) subjecting the cells to a test agent;
    (c) determining whether the test agent has activated the ROR2 receptor.

11. The method of claim 10 wherein the cells are obtained from an animal.

12. The method of claim 11 wherein the cells are chondrocytes.

13. The method of claim 11 wherein the cells are obtained by transfecting cells that normally do not express the ROR2 receptor with the ROR2 receptor nucleic acid under conditions in which the cell expresses the ROR2 receptor protein on the cell surface.

14. The method of claim 10 wherein determining whether the ROR2 receptor has been activated is accomplished by measuring phosphorylation of the receptor.

15. The method of claim 10 wherein determining whether the ROR2 receptor has been activated is accomplished by measuring chondrocyte growth, development or activity.

16. A method of identifying an agent capable of activating the ROR2 receptor comprising:
    a) obtaining chondrocytes from a normal animal;
    b) obtaining chondrocytes from an animal in which the ROR2 receptor has been mutated;
    c) contacting the chondrocytes of (a) and (b) with a test agent to determine whether the test agent is capable of activating the ROR2 receptor, wherein the determination is accomplished by comparing the activation of the ROR2 receptor of (a) with the activation of the ROR2 receptor of (b) wherein the presence of receptor activation in (a) and the absence of receptor activation in (b) is indicative of an agent capable of activating ROR2 receptor.

17. A method of preventing chondrocyte growth, development and activity comprising contacting chondrocytes expressing a ROR2 receptor with an agent capable of blocking activation of the ROR2 receptor.

18. A method of preventing cartilage formation comprising contacting chondrocytes expressing a ROR2 receptor with an agent capable of preventing chondrocyte growth, development and activity by binding to but not activating the ROR2 receptor.

19. The method of claim 17 or 18 wherein the agent is a neutralizing antibody.

20. The method of claim 19 wherein the neutralizing antibody is a monoclonal antibody.

21. The method of claim 20 wherein the monoclonal antibody is a wholly human monoclonal antibody.

22. The method of claims 17 or 18 wherein the agent is a ligand of the ROR2 receptor.

23. The method of claims 22 wherein the ligand is a naturally occurring ligand of the ROR2 receptor.

24. The method of claim 17 or 18 wherein the agent is a small molecule.

25. A method of identifying an agent capable of blocking activation of the ROR2 receptor comprising:
    (a) obtaining cells expressing the ROR2 receptor;
    (b) subjecting the cells to a test agent;
    (c) determining whether the test agent has blocked activation of the ROR2 receptor.

26. The method of claim 25 wherein the cells are obtained from an animal.

27. The method of claim 26 wherein the cells are chondrocytes.

28. The method of claim 25 wherein the cells are obtained by transfecting cells that normally do not express the ROR2 receptor with the ROR2 receptor nucleic acid under conditions in which the cell subsequently expresses the ROR2 receptor protein on the cell surface.

29. The method of claim 25 wherein determining whether the ROR2 receptor activation has been blocked is accomplished by measuring phosphorylation of the receptor.

30. The method of claim 25 wherein determining whether the ROR2 receptor activation has been blocked is accomplished by measuring chondrocyte growth, development or activity.

31. An agent identified by the method of claim 10, 16, or 25.

* * * * *